United States Patent [19]

Dailey et al.

[11] Patent Number: 4,604,198

[45] Date of Patent: Aug. 5, 1986

[54] MULTICARTRIDGE CHROMATOGRAPHY CARTRIDGE HOUSING

[75] Inventors: Nils Dailey; Vishva Rai, both of Wallingford; Kenneth Southall, Westerfield; Timothy J. Webster, Norfolk, all of Conn.

[73] Assignee: AMF Inc., White Plains, N.Y.

[21] Appl. No.: 611,662

[22] Filed: May 18, 1984

[51] Int. Cl.$^4$ .............................................. B01D 15/08
[52] U.S. Cl. ..................................... 210/198.2; 55/386
[58] Field of Search ........................ 210/198.2; 55/386

[56] References Cited

U.S. PATENT DOCUMENTS

| | | | |
|---|---|---|---|
| 3,922,223 | 11/1975 | Burkhartsmeier | 210/198.2 |
| 3,926,809 | 12/1975 | Jones | 210/198.2 |
| 4,079,009 | 3/1978 | Seiler | 210/198.2 |
| 4,259,186 | 3/1981 | Boeing et al. | 210/198.2 |
| 4,424,127 | 1/1984 | Roeraade | 210/198.2 |

*Primary Examiner*—John Adee
*Attorney, Agent, or Firm*—Ostrolenk, Faber, Gerb & Soffen

[57] ABSTRACT

A multicartridge chromatography cartridge housing for use in supporting several chromatography cartridges in a parallel array is disclosed. A number of elongated cylindrical cartridge holders extend between a lower support plate and an upper support plate. Each such cartridge holder receives a chromatography cartridge which is held within the holder by suitable end caps and tie rods. Several truss rods serve to space the support plates from each other and to support the housing assembly. Fluid flow manifolds are secured to the lower and upper support plates and serve to distribute the fluid to, and consolidate the fluid received from the cartridges within the individual holders. The multicartridge chromatography cartridge housing in accordance with the present invention handles high fluid flow volumes with a small pressure drop and with a minimum hold up volume.

20 Claims, 4 Drawing Figures

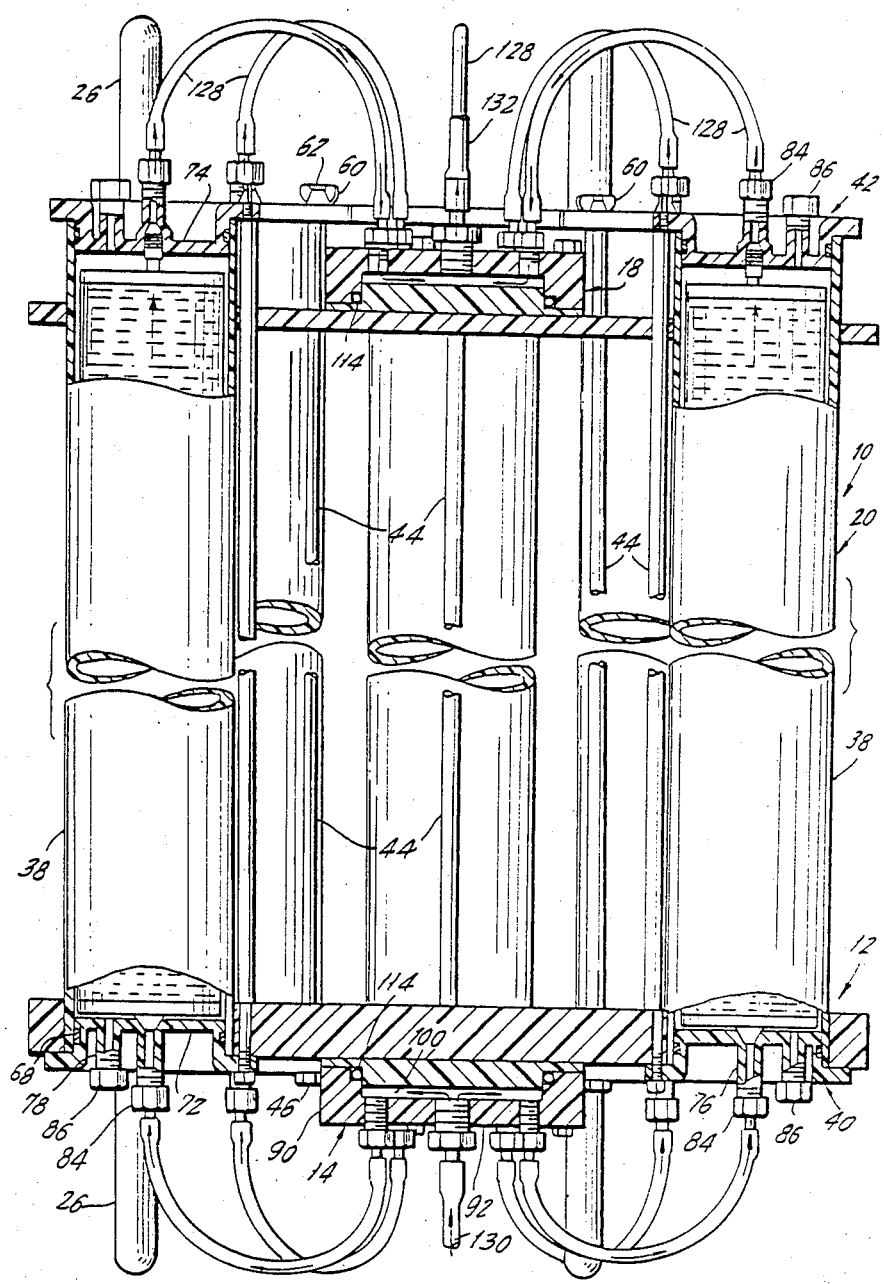

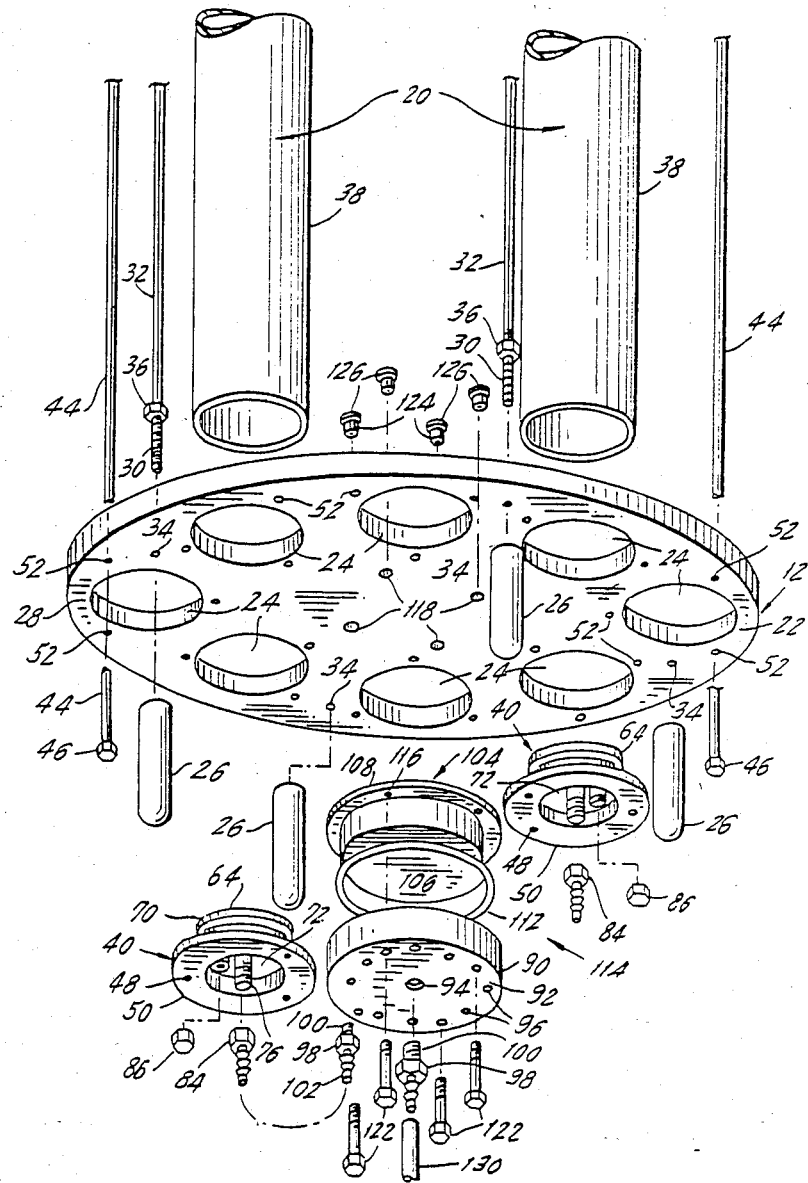

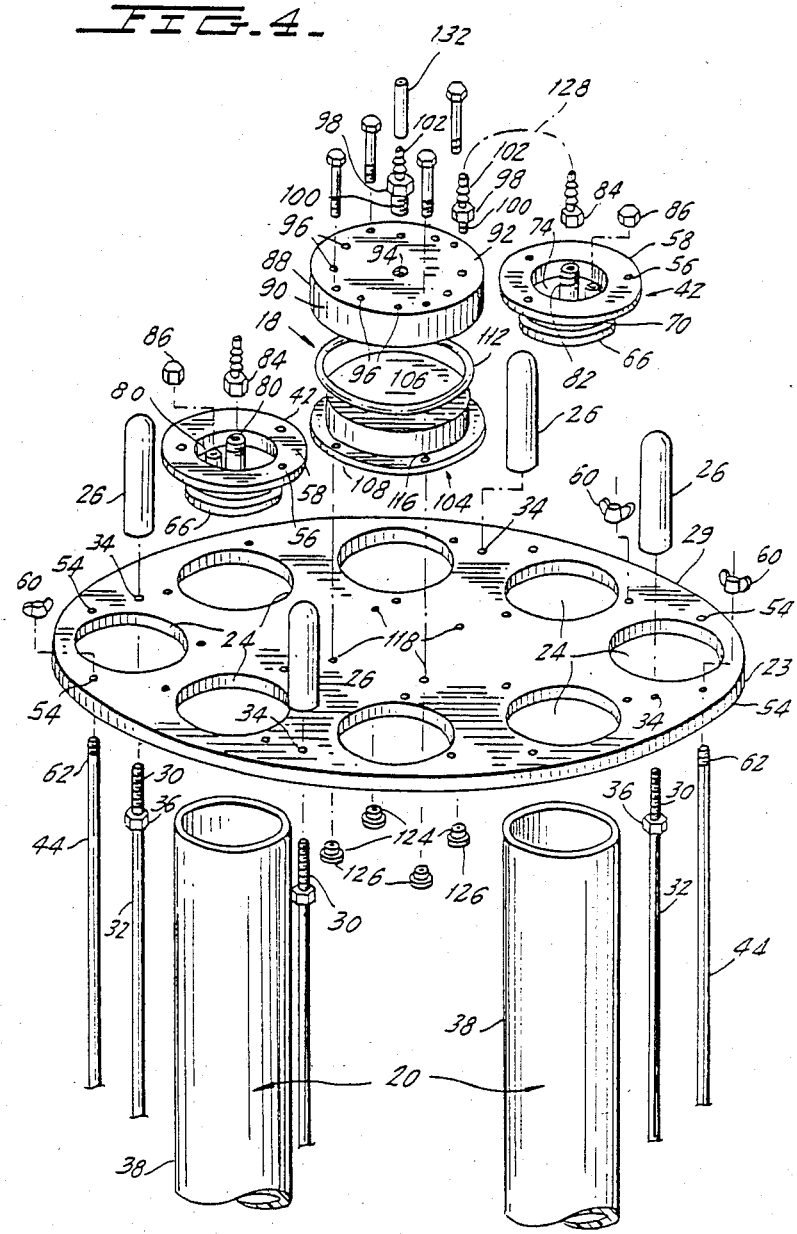

MULTICARTRIDGE CHROMATOGRAPHY CARTRIDGE HOUSING

FIELD OF THE INVENTION

The present invention is directed generally to a multicartridge housing. More particularly, the present invention is directed to a multicartridge housing for use in chromatography. Most specifically, the present invention is directed to a multicartridge chromatography cartridge housing which carries a plurality of chromatography cartridges in an assembly that facilitates a high fluid volume flow rate with a low pressure drop and a small fluid hold up volume. Preferably, a plurality of elongated cylindrical chromatography cartridge holders, which receive chromatography cartridges, are secured in parallel between spaced lower and upper support plates. The several holders are arranged in a generally cylindrical manner about central fluid inlet and outflow manifolds which are secured to the lower and upper support plates, so that multiple parallel and/or series fluid flow paths are provided through the chromatography cartridges positioned within the holders. The sizes of these holders can be varied to accept various sized cartridges which may be required by the usage intended for the chromatography apparatus.

DESCRIPTION OF THE PRIOR ART

The techniques of chromatography are generally well known in the art. Chromatography is used as a separation technique in which either a liquid or a gas is passed through a separation medium, for separation into constituent phases. The moving phase, which is either the liquid or gas, is brought to, and caused to flow through the stationary phase where separation takes place. A liquid chromatography column and a supporting housing therefor is shown in U.S. Pat. No. 3,349,920 to Waters. A preparative column assembly for gas chromatography may be seen in U.S. Pat. No. 2,960,183 to Kelly. In this patent there is further shown the use of a plurality of columns arranged in a generally cylindrical array for serial gas flow through the plurality of columns.

Chromatography cartridges have been developed that work quite well in relatively low rate situations, see Leeke et al U.S. Ser. No. 505,532 filed on June 17, 1983 now U.S. Pat. No. 4,496,461. However, as the size of the cartridge has been increased in an attempt to produce a cartridge having increased fluid flow capabilities, problems of increasing pressure drop across the cartridge and of practical size limitations have been encountered. Media which works well in a relatively small diameter cartridge suitable for low fluid flow volumes apparently does not work well in a large diameter cartridge such as would be necessary for higher flow volumes due to a change in fluid flow characteristics. As the diameter of the cartridge increases, generally the associated pressure drop through the cartridge also increases. Various previous attempts have been made to develop a single, large diameter chromatography cartridge which will provide the high fluid flow rates required for preparation and/or production chromatography without the associated high pressure drop. However, it would appear that the media currently used for these cartridges cannot function satisfactorily in such large diameter applications. The pressure drops caused by the structure of the large diameter columns which have been tried experimentally have been unacceptably high. It accordingly appears that the solution to the need for a high flow rate, low pressure drop assembly for use in chromatographic separation does not reside in the provision of a large diameter chromatography cartridge using the media currently available.

One proposed solution to the problem of obtaining an assembly capable of handling high flow rates with low pressure drops has been to attempt to place several smaller chromatography cartridges in a large housing. The fluid flow path in these cartridges is radially inwardly from the periphery to, and out through a central tube or core. A plurality of cartridges could thus be placed in a large holder or tank and the fluid flowed therethrough. This solution is not satisfactory because it results in a high hold up fluid volume; i.e., a high volume of fluid which is retained in the tank or housing and which does not pass through the chromatography cartridges. Any such hold up fluid may be wasted and the waste of a large volume of such fluid is unacceptable or undesirable from a procedural point of view. Thus the placement of plural cartridges in a large tank to overcome the high pressure drop created by a single large cartridge is also not an acceptable solution to the need for a high flow volume assembly due to the high hold up volumes such a solution produces.

A related problem with attempts to provide chromatography assemblies suitable for use in preparative and production chromatography has been a lack of adaptability to varying flow requirements. In typical useage, it is desirable to have a chromatographic assembly which will be adaptable to a wide range of flow rates and volumes. While this can be accomplished by using various sizes of column assemblies in accordance with the flow rates or volumes encountered, such a solution, which necessitates the purchase and storage of several columns of varying sizes, is not ideal and further the flow dynamics within each column can vary requiring different process parameters and associated development thereof.

A need exists for a chromatography cartridge assembly which will be efficient in operation for the large flow rates and volumes necessary in preparative and production chromatography, which will be adaptable to the widely varying flow and capacity requirements placed on it in a typical application, and which will handle high fluid flow rates while not creating large pressure drops or high hold up volumes.

SUMMARY OF THE INVENTION

It is an object of the present invention to provide a multicartridge housing for use in chromatography.

Another object of the present invention is to provide a multicartridge chromatography assembly which is efficient at large flow rates yet has a relatively low pressure drop.

A further object of the present invention is to provide a multicartridge chromatography cartridge housing which insures uniform fluid flow distribution and a low hold up fluid volume.

Yet another object of the present invention is to provide a multicartridge chromatography cartridge housing which is adjustable to a wide range of flow rates.

Still a further object of the present invention is to provide a multicartridge housing which is durable and not expensive.

A still further object of the present invention is to provide a multicartridge chromatography cartridge housing which is easy to use and maintain and which does not require complex assembly or user skill.

These and further objects are accomplished by the multicartridge housing for chromatography cartridges in accordance with the present invention. As will be set forth in greater detail in the description of the preferred embodiment, the multicartridge housing of the present invention is comprised generally of a plurality of elongated cylindrical holders, each of which is sized to accept a chromatography cartridge or cartridges which is sized to provide a low pressure drop across the cartridge, with each holder being dimensioned to afford a low hold up volume. The several elongated tubular holders are positioned adjacent and parallel to each other by upper and lower support plates to form the multicartridge housing. Suitable inlet and outlet manifold assemblies are carried by the support plates and act to deliver the fluid to, and remove the fluid from the several cartridges in a desired flow pattern.

The arrangement of plural individual cartridge holders cooperatively joined together to form the multicartridge chromatography cartridge housing in accordance with the present invention provides the previously mutually exclusive results of high fluid flow rate capabilities with low pressure drops and low fluid hold up volumes. Instead of attempting to increase the size of each individual chromatography cartridge to provide increased flow capabilities, with this solution's previously discussed limitations, the multicartridge housing in accordance with the subject invention utilizes plural cartridges, each carried in a separate holder. An inlet manifold assembly evenly divides the fluid flow between the several cartridges and an outflow manifold recombines the fluid flows exiting the several cartridges. Thus the low pressure drops of the several individual cartridges are maintained while the assembly provides the high fluid flow volumes required.

Each of the elongated tubular cartridge holders is selected and sized so that its internal diameter is only slightly larger than the outer diameter of the chromatography cartridge which it receives. In this way, the hold up volume is kept at a minimum since almost all of the fluid in each such holder is received in the chromatography cartridge. In effect, the volume for the hold up of the fluid is in fluid communication with the cartridge to enable the radial distribution of the fluid through the cartridge. In a similar fashion, the lengths of tubing which connect the fluid distribution manifolds with the individual holders are kept as short as possible by placement of the flow distribution manifolds adjacent the holders thereby keeping residual fluid volumes at a minimum level.

The multicartridge housing for chromatographic cartridges in accordance with the present invention also affords the user a high degree of flexibility with regard to various fluid flow rate requirements. This can be accomplished in either of two ways. In one alternative not all of the individual cartridge holders need receive fluid flow since one or more of the flow lines from the inlet manifold can be closed off. The lengths of the holders within which the cartridges are placed can also be varied by substitution of holders of different lengths and the placement therein of various length chromatography cartridges. For example, in the preferred embodiment, eight hollow tubular holders, each of which receives three stacked chromatography cartridges, are provided. By either stopping fluid flow to one or more of the tubular holders, or by using tubular holders sized to accept cartridges of different lengths, the fluid flow rates and volumes can be varied in response to flow requirements.

The multicartridge chromatography cartridge housing in accordance with the present invention can thus be seen to provide an assembly which affords the user the ability to handle high fluid flows with low pressure drops and with minimum fluid hold up volumes and at the same time provides an apparatus that is flexible enough so that various ranges of flow rates can be accommodated with a minimum amount of equipment without varying the flow characteristics through each cartridge.

BRIEF DESCRIPTION OF THE DRAWINGS

With the novel feature of the multicartridge chromatography cartridge housing in accordance with the present invention are set forth with particularity in the appended claims, a full and complete understanding of the invention may be had by referring to the description of a preferred embodiment, as set forth hereinafter, and as may be seen in the accompanying drawings in which:

FIG. 2 is a vertical longitudinal cross-sectional view of the multicartridge housing taken along line 2—2 of FIG. 1;

FIG. 3 is a fragmentary exploded perspective view of the lower support plate and lower, inlet manifold portion of the multicartridge housing of the present invention; and FIG. 4 is a fragmentary exploded perspective view of the upper support plate and upper, outlet manifold portion of the multicartridge housing of the present invention.

DESCRIPTION OF THE PREFERRED EMBODIMENT

Figure 1:
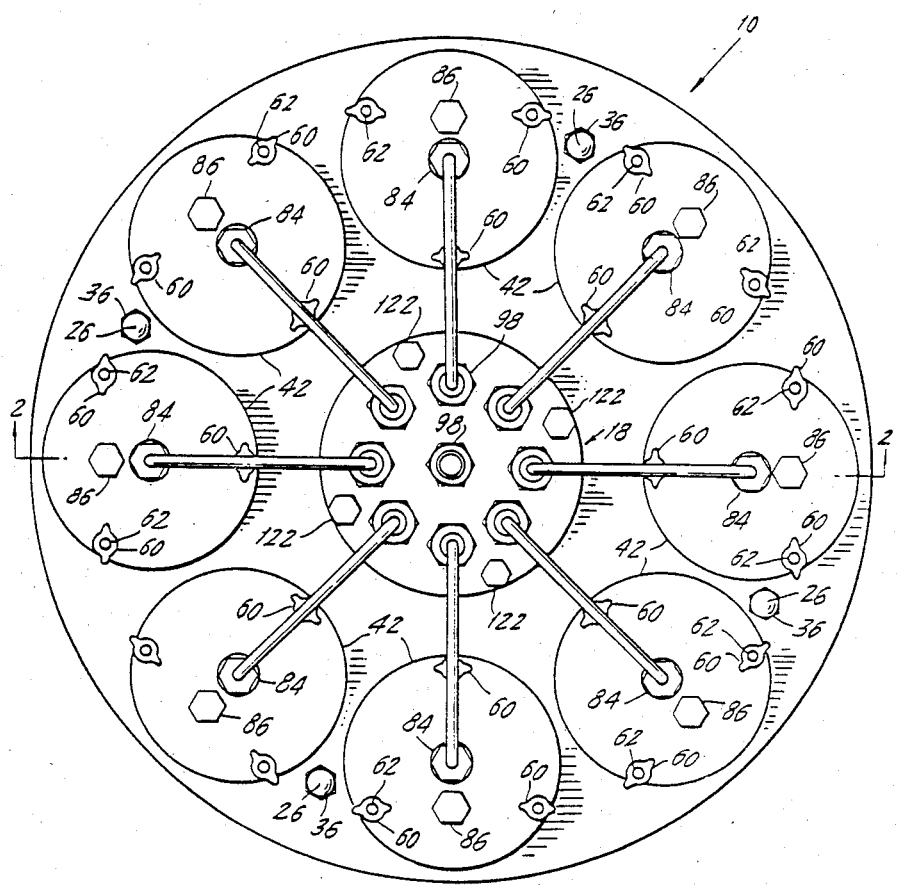
FIG. 1 is a plan view of an upper end of the multicartridge chromatography cartridge housing in accordance with the present invention and showing the flow conduits between the central manifold and the individual chromatography cartridge holders.

Referring initially to FIG. 2, there may be seen generally at 10 a preferred embodiment of a multicartridge chromatography cartridge housing in accordance with the present invention. Housing 10 is comprised generally of a lower support plate 12, a fluid inlet manifold 14 secured to lower support plate 12, an upper support plate 16, a fluid outlet manifold 18 secured to upper support plate 16, and a plurality of chromatography cartridge holders 20 which extend between the lower and upper support plates, 12 and 16 respectively. While these elements will be discussed individually in greater detail hereinafter, in operation generally a fluid to be subjected to chromatographic separation flows into inlet manifold 14 where it is evenly distributed to the several chromatography cartridges carried within the several cartridge holders 20. The fluid flows from the periphery of each cartridge to its center, in a generally known manner and exits the top of each cartridge, although the flow may be reversed to cause flow from the center to the periphery. The fluid flow from the several cartridges are combined in the outflow manifold 18 and leave the assembly. As was discussed previously, this flow pattern reduces cartridge pressure drops and hold up volumes created by larger diameter cartridges while still providing the high flow capabilities dictated by production chromatography requirements. It should be realized that the cartridges in the several cartridge holders 20 may also be manifolded to each other to provide various combinations of parallel and series flow.

Referring again to FIG. 2 in conjunction with FIGS. 3 and 4, the lower and upper support plates 12 and 14 of the multicartridge chromatography cartridge housing will now be discussed in greater detail. As seen in FIGS. 1, 3, and 4, lower and upper support plates 12 and 14 are generally in the shape of flat disks 22 and 23, respectively, which include, in the preferred embodiment, eight cartridge holder receiving apertures 24 that are equally spaced about the peripheries of disks 22 and 23. It will be understood that while eight cartridge holders 20 and their associated structure will be discussed throughout the application, that this number is exemplary of any desired number of holders 20 which could be utilized. Each disk 22 and 23 is preferably formed of an inert material such as any one of a number of compounds that are well known. A plurality of support legs 26 are positioned beneath the lower surface 28 of lower support disk 22 and above the upper surface 29 of upper support disk 23. Each of these support legs 26 is internally threaded and receives the threaded end 30 of a truss rod 32 which passes through a truss rod hole 34 in plates 22 and 23. Spacer nuts 36 are carried on each truss rod 32 and, as seen in FIGS. 3 and 4, serve to space the lower and upper support plates 12 and 16 when the housing 10 is assembled.

Each of the chromatography cartridge holders 20 is an elongated, inert, preferably transparent cylinder 38, with each such cylinder 38 being closed by lower and upper end caps 40 and 42 respectively. These end caps 40 and 42 are held on the ends of cylinders 38 by suitable elongated tie rods 44. Each such tie rod 44 carries a conventional nut 46 or alternatively may have a bolt head integrally formed on its lower end. Each of the tie rods 44 passes through a bore 48 formed in a flange 50 of lower end cap 40, thence through a cooperatively positioned hole 52 in lower support plate 12, which hole 52 is formed adjacent a cartridge holder receiving aperture 24, and upwardly through a corresponding hole 54 in upper support plate 16, as seen in FIG. 4. The tie rod 44 then passes through a bore 56 in a flange portion 58 of an upper end cap, generally at 42. A suitable securement means such as a wing nut 60 is then placed on a threaded upper end 62 of each tie rod 44 and is tightened down against the upper surface of flange 58. As can be seen most clearly in FIG. 1, each upper end cap 42 is held on to the upper end of the elongated transparent cylinder 38 of each chromatography cartridge holder 20 by three such tie rods and wing nuts 60. This three point securement insures that each end cap 40 or 42 is securely held in place on the ends of each cylinder 38.

As is shown in FIG. 3 for lower end caps 40, and in FIG. 4 for upper end caps 42, each of the end caps 40, 42 includes the peripheral flange 50, 58, as previously discussed, and a reduced diameter cylinder wall portion 64, 66 which enters the bore of the elongated transparent cylinder 38, as may be seen in FIG. 2. A suitable gasket means such as a resilient O-ring 68 is placed in a ring groove 70 formed in side walls 64 and 66 of lower and upper end caps 40 and 42, respectively. A leak proof seal is thus formed betwen the side walls 64, 66 of the end caps 40 and 42 and the ends of the cylinders 38 due to the close dimensional tolerances maintained during manufacture and because of the use of the O-ring gaskets 68.

Each end cap 40, 42 has a flat end wall portion 72, 74 which is formed at the terminus of the side walls 64, 66 remote from flanges 50, 58, respectively. Each of these end walls 72, 74 is provided with a central hollow nozzle 76 and a radially outwardly offset nozzle 78. The terminal ends 80 each of these nozzles 76 and 78 are provided with external threads 82. A hose adapter 84 is attached to the threaded end 80 of each of the central nozzles 76 while a closure cap 86 is attached to the terminal end of each of the offset nozzles 78.

As was alluded to previously, inlet and outlet manifolds 14 and 18 are attached to the lower and upper support plates 12 and 16 respectively. These manifolds are the same in structure, but have differing flow direction patterns as will be discussed shortly. Each manifold assembly 14, 18 includes a generally cup-shaped body element 88 which includes cylindrical side walls 90 that terminate at one end in a planar web 92 which is provided with a cenral threaded aperture 94 and eight equally radially spaced threaded apertures 96. Each one of these threaded apertures 94 and 96 receives a threaded hose adaptor 98 that has suitable male threads 100 on one end, and a ribbed, hose engaging extension 102 on the second end.

A closure plate 104 for each manifold assembly 14 and 18 has a central plug 106, which is received within the cup shaped body element 88, and an enlarged flanged lip 108. The thickness of plug 106 is less than the height of the side walls 90 of the cup shaped element 88 to thereby define a fluid chamber 110 when the cup-shaped body element 88 and closure plate 104 are assembled. A suitable O-ring 112 is placed in an O-ring groove defined by outwardly sloping portions 114 of the inner free ends of the cylindrical side walls 90 of the cup shaped element 88.

Each of the manifold assemblies 14 and 18 are secured to their respective support plates 12 and 16 by placement of the enlarged, flanged lip 108 against a central portion of the respective support plate 12, 16 so that holes 116 in the lip 108 are aligned with cooperatively spaced holes 118 in the support plates 12, 16. The O-ring 112 is then set in the O-ring groove 114 and the cup-shaped body element 88 is placed on the closure plate 104. The cup shaped element 88 is also provided with bolt receiving holes 120 which are aligned with the holes 116 in the enlarged flanged lip 108 and with the holes 118 in the support plates 12 and 16. Suitable bolts 122 are then passed through these aligned holes and are threaded into cooperative internally threaded retainer nuts 124 having enlarged heads 126. These retainer nuts 124 are, as seen in FIGS. 3 and 4, positioned against the inner sides of the support plates 12 and 16 and are prevented from passing therethrough due to their enlarged heads 126.

In use and assembly, a chromatography cartridge generally of the type set forth in the Leeke et al application Ser. No. 505,532, filed June 17, 1983 and assigned to a common assignee, is placed within each one of the elongated hollow cylinders 38. Each cylinder 38 is then placed in an aperture 24 in the lower support plate 12 and a lower end cap 40 is inserted in the lower end of the cylinder 38. It will facilitate assembly of the housing if the truss rods 32 and lower support legs 26 have already been attached to the lower support plate 12. Once all eight of the cylinders 38 are in place, the upper support plate 16 is lowered over the upper ends of the cylinders 38 and the truss rods 32 until the inner surface of the upper support plate 18 rests on the upper spacer nuts 36. The upper end caps 42 can then be positioned about each cylinder 38. Three tie rods 44 are then positioned about each cylinder 38, passing through apertures 48 in the lower end cap 40, tie rod holes 52 and 54 in the lower and upper support plates 12 and 16, and through apertures 56 in the upper end caps 42. Wing nuts 60 are then applied to the free upper ends of the tie rods 44 and the upper support feet 26 are secured to the upper ends of the truss rods 32. If not previously attached, the manifold assemblies 14 and 18 are secured to the lower and upper support plates 12 and 16, respectively. Suitable hose members 128 are then connected between the peripheral hose adaptors 98 on the manifolds 14 and 18 and the individual hose adaptors 84 on the end caps 40 and 42, respectively. The closure caps 86 which are attached to the offset nozzles 78 on the end caps 40 and 42 provide vent and drain means during filling and draining of the cylinders 38 and are closed at other times. The multicartridge chromatography cartridge housing is now ready for use and this is accomplished by attachment of a fluid infeed hose 130 to the hose adaptor 98 secured in the central aperture 94 of the inlet fluid manifold 14, and by attachment of an outflow hose 132 to the hose adaptor 98 secured in the central aperture 94 of the outlet manifold assembly 18. Fluid can then flow in the direction indicated by the flow arrows shown in FIG. 2; i.e., centrally into fluid chamber 110 in inlet manifold 14, radially outwardly through hoses 128 to the lower end caps 40, up and through each of the chromatography cartridges contained in each of the elongated cylinders 38, out through the upper end caps 42, radially inwardly through upper hoses 128 to the outflow manifold 18 carried on upper support plate 16, through fluid chamber 110 in outflow manifold 18 and centrally out through outlet hose 132.

As discussed previously and as can now be understood in light of the above description of the preferred embodiment, the multicartridge chromatography cartridge housing in accordance with the present invention facilitates the previously mutually exclusive goals of low cartridge pressure drops with large flow volumes, and constant cartridge flow characteristics. Each cartridge is small enough to work efficiently with a low pressure drop, and the multiple parallel flow paths afforded by the subject structure provides the high flow rates and volumes required in numerous uses. it will be understood that the flow rates can be varied if desired by, for example, eliminating one or more of the individual cartridges and its associated holder 38 from the flow path. This can easily be done by capping off the required number of peripheral hose adaptors 98 at the manifolds. Since the manifolds are self-proportioning the flow will be equally distributed among the cartridges and holders still connected to the manifolds. Alternatively, the lengths of the holders 44 could be changed and cartridges of different lengths could be used. Also, while an arrangement of eight cartridge holders 44 has been disclosed and described, it will be apparent that this could be varied. The flow characteristics through the cartridges whether in series or parallel can also be used to vary flow.

While a preferred embodiment of a multicartridge chromatography cartridge housing in accordance with the present invention has been fully and completely described hereinabove, it will be obvious to one of skill in the art that a number of change in, for example, the materials used, the various fastening means, the connectors and the like could be made without departing from the true scope and spirit of the invention and that the invention is accordingly to be limited only by the following claims.

We claim:
1. A multicartridge housing for cylindrical chromatographic cartridges, each cartridge effective for the chromatographic separation of a fluid passing radially therethrough, said housing comprising:
   support means;
   a plurality of cartridge holders secured to said support means, each of said cartridge holders being structured and sized to surround a cartridge therein and a volume surrounding the cartridge, said volume in fluid communication with said cartridge for radial distribution of the fluid through the cartridge;
   an inlet fluid manifold means for distributing the fluid being separated to each of said holders for passage of the fluid radially through the cartridges therein; and
   an outlet fluid manifold means for consolidating the fluid from the holders after passage of the fluid radially through the cartridges therein.
2. The multicartridge housing in accordance with claim 1 wherein said support means includes lower and upper support plates.
3. The multicartridge housing of claim 2 wherein said lower and upper plates include a plurality of cartridge holder receiving apertures.
4. The multicartridge housing of claim 3 wherein said cartridge holders are elongated cylinders extending between said lower and upper plates and being secured in said cartridge holder receiving apertures.
5. The multicartridge housing in accordance with claim 1 wherein each of said cartridge holders includes an elongated hollow cylinder closed at its ends with end caps.
6. The multicartridge housing of claim 5 wherein each of said end caps includes a cylindrical wall portion receivable within an end of said cylinder and a flange extending radially outwardly from said wall portion at a first end thereof.
7. The multicartridge housing in accordance with claim 6 wherein said cylindrical wall portion of each of said end caps includes an O-ring receiving groove.
8. The multicartridge housing of claim 6 wherein each of said end caps is held in said ends of said cartridge holders by tie rods.
9. The multicartridge housing of claim 8 wherein said tie rods pass through tie rod receiving bores in said flanges.
10. The multicartridge housing in accordance with claim 5 wherein said end caps include fluid flow nozzles.
11. The multicartridge housing of claim 10 wherein each of said end caps includes two fluid flow nozzles.
12. The multicartridge housing of claim 11 wherein a first of said fluid flow nozzles terminates in a hose adaptor and a second of said fluid flow nozzles on each of said end caps receives a closure cap.
13. The multicartridge housing in accordance with claim 2 wherein said lower and upper support plates are spaced from each other by truss rods which extend between, and pass through said lower and upper support plates.
14. The multicartridge housing in accordance with claim 13 wherein support legs are secured to ends of said truss rods and extend generally perpendicularly of, and outwardly from said lower and upper support plates.

15. The multicartridge housing of claim 1 wherein each of said manifolds includes a generally cupshaped body element and a cooperating closure plate.

16. The multicartridge housing of claim 15 wherein said closure plate includes a central plug which is disposed within said cup shaped body element and which cooperates therewith to define a fluid chamber when said cup-shaped body element and said closure plate are assembled to form said manifold.

17. The multicartridge housing of claim 16 wherein said cup-shaped element includes a planar web defining the base of said cup-shaped element.

18. The multicartridge housing of claim 17 wherein said planar web includes a central aperture and a plurality of radially spaced apertures, each of said apertures being in fluid communication with said fluid chamber and receiving a threaded hose adaptor.

19. The multicartridge housing of claim 18 wherein said central aperture is connected to a fluid inflow or outlet line and wherein each of said radially spaced apertures is connected to one of said cartridge holders.

20. The multicartridge housing in accordance with claim 1 wherein said inlet fluid manifold and said outlet fluid manifold are secured to said support means.

* * * * *